United States Patent [19]

Sato

[11] 4,239,709
[45] Dec. 16, 1980

[54] PROCESS FOR PREPARING OPTICALLY ACTIVE OXAZAPHOSPHORINS

[75] Inventor: Tadao Sato, Tokushima, Japan

[73] Assignee: Otsuka Pharmaceutical Co., Ltd., Tokyo, Japan

[21] Appl. No.: 43,462

[22] Filed: May 29, 1979

[30] Foreign Application Priority Data

May 29, 1978 [JP] Japan .................................. 53-64681

[51] Int. Cl.$^3$ .............................................. C07F 9/24
[52] U.S. Cl. ..................................... 260/974; 260/936
[58] Field of Search .............................. 260/936, 974

[56] References Cited

U.S. PATENT DOCUMENTS 3,732,340  5/1973  Arnold et al. ........................ 260/936

FOREIGN PATENT DOCUMENTS 1203268 10/1965 Fed. Rep. of Germany ............ 260/936
1235022  6/1971 United Kingdom ..................... 260/936

OTHER PUBLICATIONS

Iwamoto, et al., "J. Org. Chem.", vol. 26, (1961), pp. 4743-4745.

*Primary Examiner*—Anton H. Sutto
*Attorney, Agent, or Firm*—Finnegan, Henderson, Farabow, Garrett & Dunner

[57] ABSTRACT

Novel method optically active oxazaphosphorin derivatives represented by the general formula (I),

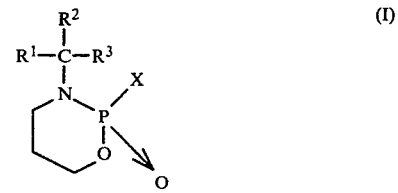

wherein $R^1$, $R^2$ and $R^3$ are respectively different from each other and are hydrogen atom(s), lower alkyl group(s), aralkyl group(s), or aryl group(s); and X is a halogen atom. The novel oxazaphosphorin derivative is prepared by reacting an optically active amino alcohol derivative represented by the general formula (II),

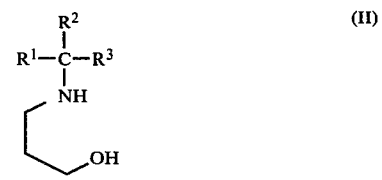

wherein $R^1$, $R^2$ and $R^3$ are the same as defined above, with a phosphorus compound represented by the general formula (III), $$POX_3$$

wherein X is the same as defined above.

The novel optically active oxazaphosphorin derivatives are useful as intermediates for preparing optically active cyclophosphamide derivatives which are useful therapeutic agents for curing against follicular lymphoadenopathy, lymphosarcomatosis, Hodgkin's disease, lymphosarcoma cell leukaemia, reticulum-cell sarcoma or the like.

14 Claims, No Drawings

PROCESS FOR PREPARING OPTICALLY ACTIVE OXAZAPHOSPHORINS

Present invention relates to a novel method for preparing novel optically active oxazaphosphorin derivatives.

The novel optically active oxazaphosphorin derivatives of the present invention are represented by the general formula (I),

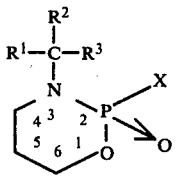

wherein $R^1$, $R^2$ and $R^3$ are respectively different from each other and are hydrogen atom, a lower alkyl group, aralkyl group or aryl group; and X is a halogen atom, which are prepared by reacting an optically active amino alcohol represented by the general formula (II),

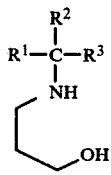

wherein $R^1$, $R^2$ and $R^3$ are the same as defined above, with a phosphorus compound represented by the general formula (III), $$POX_3 \qquad (III)$$

wherein X is a halogen atom.

The novel optically active oxazaphosphorin derivatives represented by the general formula (I) are useful intermediates for preparing optically active cyclophosphamide which are useful therapeutic agents for curing against follicular lymphoadenopathy, lymphosarcomatosis, Hodgkin's disease, lymphosarcoma-cell leukaemia, reticulum-cell sarcoma and the like.

The optically active amino alcohol derivatives represented by the general formula (II) used as the starting material in the present invention are known compounds and are easily prepared by methods as described in prior art literatures [for example, Gerald Zon, Tetrahedron Letters, No. 36, pages 3139–3142 (1975); T. Kawashima, et al., J. Org. Chem., 43, pages 1111–1114 (1978); German Patent Offenlegungsschrift No. 2,644,905].

Amino alcohol of the general formula (II) has one asymmetric carbon atom in its molecule, thus the compound represented by the general formula (II) includes R-amino alcohol derivative and S-amino alcohol derivative. The lower alkyl group as defined in the symbols $R^1$, $R^2$ and $R^3$ in the general formula (II) contain methyl, ethyl, n-propyl, isopropyl, n-butyl, tert-butyl or the like. The aryl group as defined in the symbols $R^1$, $R^2$ and $R^3$ in the general formula (II) may have substituent(s) in the aryl group ring and aryl ring of the aralkyl group. The examples of such substituents are electron donating groups for example lower alkyl group, lower alkoxy group such as methoxy group or ethoxy group; lower alkylenedioxy group such as methylenedioxy group or ethylenedioxy group; halogen atom such as chlorine atom, bromine atom.

Examples of the aryl groups are phenyl group, p-methylphenyl group, p-methoxyphenyl group, o-methylphenyl group, 3,4-dimethoxyphenyl group, p-chlorophenyl group, 3,4-methylenedioxyphenyl group, α-naphthyl group, β-naphthyl group and the like.

Compounds represented by the general formula (III) which are used as another starting material in the present invention are known compounds. The halogen atom as defined in the symbol X in the general formula (III) includes chlorine atom, bromine atom, iodine atom and the like.

In the reaction of a compound of the general formula (II) with a compound of the general formula (III), the ratio of both compounds to be used is not specifically limited and can be selected from a wide range. Generally, the latter is used at least an equimolar quantity to 3 times molar quantity of the former, preferably an equimolar to 1.5 times the molar quantity of the former. The reaction can be carried out in the absence or presence of a solvent. Any known solvent which does not give any adverse effect to the reaction can be used as the solvent. For example, halogenated hydrocarbon such as methylene chloride, chloroform or 1,2-dichloroethane; an aromatic hydrocarbon such as benzene, toluene or xylene; an ether such as dimethylether, diethylether, isopropylether, tetrahydrofuran, dioxane, 1,2-dimethoxyethane, diglyme, triglyme or the like; a saturated hydrocarbon such as n-heptane, n-hexane, cyclohexane, isooctane or the like is preferably used as the solvent. The reaction may be carried out in the absence or presence of a basic compound in the reaction system, but the reaction can preferably be carried out in the presence of the basic compound. As to the basic compound, any of known basic compound which does not give any adverse effect can be used. For example, a tertiary amine such as triethylamine, triisopropylamine, N,N-dimethylaniline, pyridine, quinoline or the like; an inorganic basic compound such as anhydrous potassium carbonate, anhydrous sodium carbonate or the like is preferably used. The amount of the basic compound to be used is not specifically limited and it can be selected from wide range. Generally, however, 2 to 5 times of molar quantity, preferably 2 to 3 times of molar quantity of the basic compound per mole of the compound of the general formula (II) can preferably be used. The reaction temperature of said reaction is not specifically limited and the reaction can be carried out at any temperature condition such as under cooling, heating or at a room temperature. Usually, the reaction can be carried out at $-70°$ to $100°$ C., preferably at $-70°$ to $50°$ C. The reaction is completed within a period of from 10 minutes to 10 hours.

The compound represented by the general formula (I) of the present invention thus prepared can easily be isolated and purified by means of recrystallization.

Since the compound represented by the general formula (I) contains one asymmetric phosphor atom and one asymmetric carbon atom in its molecule R-R-oxazaphosphorin derivative, R-S-oxazaphosphorin derivative, S-R-oxazaphoshporin derivative and S-S-oxazaphosphorin derivative are included in the compound represented by the general formula (I). In naming of the said compounds, the symbols of R and S firstly appeared show the absolute configuration of asymmetric phosphor atom and the other symbols of secondary appeared show the absolute configuration of asymmetric carbon atom.

In the present invention, when R-aminoalcohol among the compounds represented by the general formula (II) is used as the starting material, only R-R-oxazaphosphorin derivative and S-R-oxazaphosphorin derivative among the compounds represented by the general formula (I) can be obtained and one of them formed selectively in larger amounts (generally 60% or more, and usually 80% or more amounts) than another. Alternatively, when S-aminoalcohol among the compounds represented by the general formula (II) is used as the starting material, only R-S-oxazaphosphorin derivative and S-S-oxazaphosphorin derivative among the compounds represented by the general formula (I) can be obtained and one of them formed selectively in larger amounts (generally 60% or more, and usually 80% or more amounts) than another. These facts will be shown later in the examples.

The configuration of asymmetric phosphor atom can be inversed from one type thereof to another type by means of SN2-type reaction (bimolecular nucleophilic substitution) by reacting a compound represented by the general formula (I) with a nucleophilic reagent (for example, azid ion, cyanide ion, p-nitrophenoxide ion, p-nitrothiophenoxide ion or the like) which can be able to be releasing group [Reaction formula-1].

Reaction formula-1

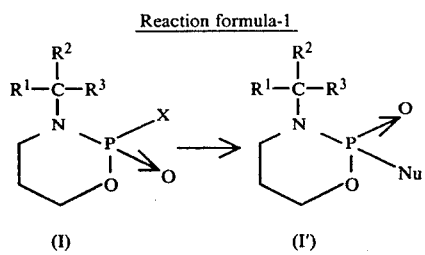

(I)    (I')

wherein Nu is azid group, cyanide group, p-nitrophenoxide group or p-nitrothiophenoxide group; $R^1$, $R^2$, $R^3$ and X are the same as defined above.

In the SN2-type substitution reaction (inversion reaction), the ratio of the quantity of a compound represented by the general formula (I) to the quantity of a nucleophilic reagent is not specifically limited and the ratio may be selected from a wide range thereof. Generally, an equimolar quantity to 5 times of quantity, preferably an equimolar quantity to 2 times of quantity of the latter (a nucleophilic reagent) per molar quantity of the former is used.

The SN2-type substitution reaction can advantageously be carried out by using an alcohol such as methanol, ethanol, propanol, butanol or the like; an ethereal solvent such as dioxane, tetrahydrofuran, 1,2-dimethoxyethane, diglyme, triglyme or the like; an aprotic polar solvent such as dimethylformamide, dimethylacetamide, dimethylsulfoxide, N-methylpyrrolidone, hexamethylphosphoryltriamide or the like. Generally the reaction can be carried out at −30° to 150° C., preferably at −10° to 100° C. The reaction is generally completed within the period of from 30 minutes to about 30 hours.

The oxazaphosphorin derivative represented by the general formula (I) obtained in accordance with the present invention can be introduced to an optically active cyclophosphoramide represented by the general formula (VII) as shown in the reaction formula-2.

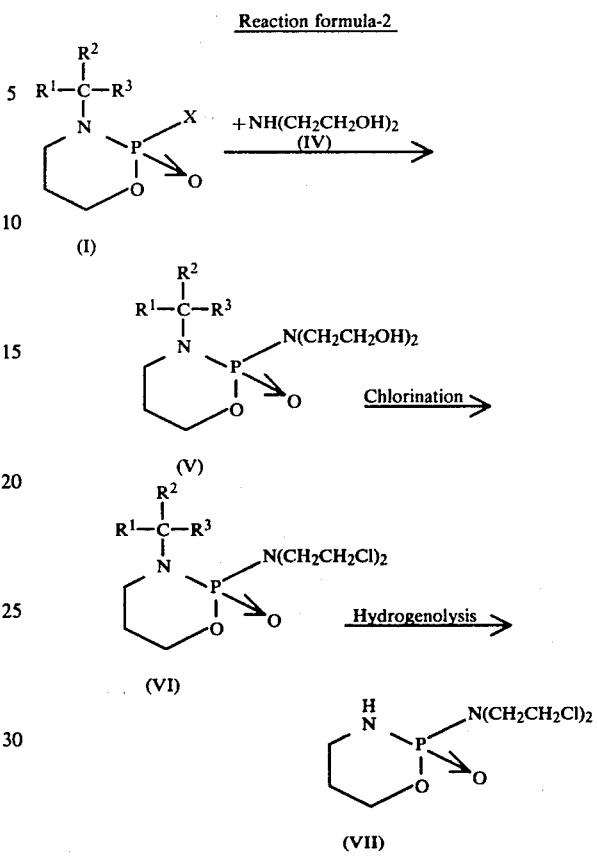

In the reaction of a compound represented by the general formula (I) with diethanolamine, the ratio of both compounds to be used is not specifically limited and can be selected from a wide range. Generally, an equimolar quantity to ten times quantity, preferably an equimolar quantity to five times quantity of the latter is used per molar quantity of the former. The reaction is carried out in the absence or presence of a solvent. As to the solvent to be used is exemplified such as water, an alcohol such as methanol, ethanol, propanol, butanol or the like; a halogenated hydrocarbon such as methylene chloride, chloroform, 1,2-dichloroethane or the like; an ethereal solvent such as diethylehter, tetrahydrofuran, dioxane, 1,2-dimethoxyethane, diglyme, triglyme or the like; an aprotic polar solvent such as dimethylformamide, dimethylacetamide, dimethylsufoxide, N-methylpyrrolidone, hexamethylphosphoryl triamide or the like. The reaction can be carried out in the absence or presence of a basic compound in the reaction system. As to the basic compound to be used is exemplified such as a tertiary amine compound for example triethylamine, N,N-dimethylaniline or the like. The reaction can be carried out at a room temperature to 200° C., preferably a room temperature to 150° C. The reaction is generally completed within a period of 30 minutes to about 10 hours.

The chlorination of a compound represented by the general formula (V) is carried out under a conventional chlorination reaction selected from a wide range by using thionyl chloride, phosphorus trichloride, phosphoroxychloride, phosphorus pentachloride, hydrochloric acid, hydrochloric acid-$ZnCl_2$, hydrochloric acid - HMPA, triphenylphosphine-carbon tetrachloride, triphenylphosphodichloride or trisdimethylaminophosphine-carbon tetrachloride as a chlorinating agent. The quantity of the chlorinating agent to be used may be an equimolar quantity to an excess quantity, preferably an equimolar quantity to five times quantity per molar quantity of a compound represented by the general formula (V). Conventional solvent which is selected from a wide range can be used as the solvent for the reaction. Examples of the solvents are halogenated hydrocarbon such as chloroform, methylene chloride, 1,2-dichloroethane or the like; ethereal solvents such as diethylether, tetrahydrofuran, dioxane, 1,2-dimethoxyethane, diglyme, triglyme or the like.

The reaction may be carried out at a room temperature to 100° C., preferably at a room temperature to 70° C. The reaction is completed within a period about 30 minutes to 6 hours.

The hydrogenolysis of a compound represented by the general formula (VI) is carried out by using a catalyst for example palladium charcoal, palladium black, platinum oxide, rhodium catalyst, Raney nickel or the like, under a catalytic hydrogenation. The catalytic hydrogenation can advantageously be carried out in a solvent such as water, methanol or ethanol at a room temperature to 100° C., preferably at a room temperature to 60° C. The reaction is usually completed within 30 minutes to about 30 hours, preferably 30 minutes to 20 hours, and the hydrogen gas pressure is usually from an atmospheric pressure to 150 atmospheres, preferably an atmospheric pressure to 100 atmospheric pressure.

After the reaction is completed, the cyclophosphamide represented by the general formula (VII) thus prepared is separated from the reaction mixture by filtration to remove insoluble matters, and the solvent used is removed by distillation to isolate the product and recrystallized from a suitable solvent selected from the group consisting of ether, ether-hexane, isopropyl ether, benzene-hexane, carbon tetrachloride-hexane, benzene-isoctane and the like. The cyclophosphamide represented by the general formula (VII) thus obtained contains (S)-(−)-cyclophosphamide and (R)-(+)-cyclophosphamide. S-(−)-cyclophosphamide has been known as a compound having excellent pharmacological activities as compared with R-(+)-cyclophosphamide [P. J. Cox, et al., Biochemical Pharmacology, vol. 25, pp. 993–996, published from Pergamon Press, 1976, printed in Great Britain].

In carrying out properly the reactions as explained the reaction formulas-1 and -2, S-(−)-cyclophosphamide can be prepared from an optical active oxazaphosphorin represented by the general formula (I) obtained by a method accoridng to the present invention. Thus S-(−)-cyclophosphamide can be prepared by any one of the following methods.

(1) A compound of S-S-form represented by the general formula (I) is inverted by applying SN2-type reaction (bimolecular nucleophilic substitution) to a compound represented by the general formula (I'), then reacting it with ethanolamine represented by the general formula (IV) to obtain a compound of R-S-form represented by the general formula (V). Then the compound of R-S-form represented by the general formula (V) is chlorinated to obtain a compound of R-S-form represented by the general formula (VI), and further it is hydrogenolyzed to obtain S-(−)-cyclophosphamide.

(2) A compound of R-S-form represented by the general formula (I) is first reacted with ethanolamine represented by the general formula (IV) to obtain a compound of R-S-form represented by the general formula (V), then it is chlorinated to obtain a compound of R-S-form represented by the general formula (VI), further hydrogenolyzed to obtain S-(−)-cyclophosphomide.

(3) A compound of R-R-form represented by the general formula (I) is reacted with ethanolamine represented by the general formula (IV) to obtain a compound of R-R-form represented by the general formula (V), then it is chlorinated to obtain a compound of R-R-form represented by the general formula (VI), further hydrogenolyzed to obtain S-(−)-cyclophosphamide.

(4) A compound of S-R-form represented by the general formula (I) is inverted by applying SN2-type reaction (bimolecular nucleophilic substitution) to a compound represented by the general formula (I'), then reacting it with ethanolamine represented by the general formula (IV) to obtain a compound of R-R-form represented by the general formula (V), and further it is hydrolyzed to obtain S-(−)-cyclophosphomide. As it is described above, S-(−)-cyclophosphomide can be prepared from any of the compound represented by the general formula (I).

Additionally, R-(+)-cyclophosphamide can be prepared from an optical active oxazaphosphorin derivative represented by the general formula (I) obtained by a method according to the present invention. Thus R-(+)-cyclophosphamide can be prepared by any one of the following (5)–(8) methods.

(5) A compound of R-R-form represented by the general formula (I) is inverted to a compound represented by the general formula (I') by applying SN2-type reaction (bimolecular nucleophilic substitution), then reacting it with ethanolamine represented by the general formula (IV) to obtain a compound of S-R-form represented by the general formula (V), then it is chlorinated to obtain a compound of S-R-form represented by the general formula (VI), and further it is hydrogenolyzed to obtain R-(+)-cyclophosphamide.

(6) A compound of S-R-form represented by the general formula (I) is first reacted with ethanolamine represented by the general formula (IV) to obtain a compound of S-R-form represented by the general formula (V), then it is chlorinated to obtain a compound of S-R-form represented by the general formula (VI), further hydrogenolyzed to obtain R-(+)-cyclophosphamide.

(7) A compound of S-S-form represented by the general formula (I) is reacted with ethanolamine represented by the general formula (IV) to obtain a compound of S-S-form represented by the general formula (V), then it is chlorinated to obtain a compound of S-S-form represented by the general formula (VI), further hydrogenated to obtain R-(+)-cyclophosphamide.

(8) A compound of R-S-form represented by the general formula (I) is inverted to a compound represented by the general formula (I') by applying SN2-type reaction (bimolecular nucleophilic substitution), then reacting it with ethanolamine represented by the general formula (IV) to obtain a compound of S-S-form represented by the general formula (V), and further it is hydrolyzed to obtain R-(+)-cyclophosphamide.

As it is described above, R-(+)-cyclophosphamide can be prepared from any of the compounds represented by the general formula (I).

According to a report made by P. J. Cox, et al., [Biochemical Pharmacology, vol. 25, pp. 993–996, (1976), Pergamon Press] as previously mentioned, the anti-tumor effect of S-(−)-cyclophosphamide against PC6-Tumor is better than those of R-(+)-cyclophosphamide and racemic form of cyclophosphamide against L 1210-Tumor (in mice) and P388-Tumor (in mice). As can be seen from pharmacological data shown below, anti-tumor effect of S-(−)-cyclophosphamide against P388-Tumor is better than those of R-(+)-cyclophosphamide and racemic form of cyclophosphamide. However, in case of testing anti-tumor effect against L 1210-Tumor which is different type of tumor, R-(+)-cyclophosphamide shows better anti-tumor effect than those of shown by S-(−)-cyclophosphamide and racemic form of cyclophosphamide. Furthermore, R-(+)-cyclophosphamide shows lower acute toxicity (in mice) than those shown by S-(−)-cyclophosphamide and racemic form of cyclophosphamide. These facts show that R-(+)-cyclophosphamide and S-(−)-cyclophosphamide have more excellent therapeutic effects than that shown by racemic form of cyclophosphamide depend on the type of tumors.

By administering any one of R-(+)- and S-(−)-cyclophosphamide, an excellent anti-tumor activity with less side-effect can be expected as compared with administering racemic form of cyclophosphamide.

Thus, any one of R-(+-cyclophosphamide and S-(−)-cyclophosphamide which are useful anti-tumor agents can be derived from a compound represented by the general formula (I) obtained by a process according to the present invention.

Anti-tumor tests (1) Method of test

Lymphocytic leukemia P388 liquid-type tumor was transplanted ($1 \times 10^6$ cells) in abdominal cavity of $BDF_1$ male mice having the body weight of about 20 g. The effect was evaluated by a method of ILS (Increase in life span).

Similarly lymphocytic leukemia P388 solid-type tumor was transplanted ($1 \times 10^6$ cells) in subcutis on the back of $BDF_1$ male mice having the body weight of about 22 g. The mice were killed 15 to 16 days after the transplantation and the inhibitory effect of tumor proliferation was evaluated by measuring the weight of tumor.

Lymphoid leukemia L-1210 solid-type tumor was transplanted ($1 \times 10^6$ cells) in subcutis on the back of $BDF_1$ male mice having the body weight of about 22 g. The mice were killed 10–11 days after the transplantation and the inhibitory effect of tumor proliferation was evaluated by measuring the weight of tumor.

Each of 5, 10, 20, 50, 100 mg of compounds to be tested is dissolved in a phisiological NaCl solution (5 mg/kg of concentration) and administered by intraperitoneal injection (I.P.) or orally (P.O.). As to the reference the phisiological NaCl solution (5 mg/kg of concentration) was used.

(2) Test results

The results obtained are shown in Table 1 and Table 2 below.

TABLE 1

| Compound tested | L1210 Tumor test | | |
|---|---|---|---|
| | Method of administration | $ID_{90}$ (mg/kg) | $ID_{50}$ (mg/kg) |
| R-(+)-cyclophosphamide | P.O. | 76 | 24 |
| | I.P. | 104 | 32 |
| S-(−)-cyclophosphamide | P.O. | 95 | 29 |

TABLE 1-continued

| Compound tested | L1210 Tumor test | | |
|---|---|---|---|
| | Method of administration | $ID_{90}$ (mg/kg) | $ID_{50}$ (mg/kg) |
| | I.P. | 143 | 44 |
| Racemic form of cyclophosphamide | P.O. | 90 | 28 |
| | I.O. | 107 | 33 |

TABLE 2

| Compound tested | P328 Tumor test | | |
|---|---|---|---|
| | Method of administration | $ID_{90}$ (mg/kg) | $ID_{50}$ (mg/kg) |
| R-(+)-cyclophosphamide | I.P. | 50.8 | 24.3 |
| S-(−)-cyclophosphamide | I.P. | 26.3 | 14.6 |
| Racemic form of cyclophosphamide | I.P. | 39.7 | 12.9 |

Acute toxicity test $LD_{50}$ (mg/kg) values (ICR male mice, I.P.) of R-(+)-cyclophosphamide, S-(−)-cyclophosphamide and racemic form of cyclophosphamide are shown below.

| Compound tested | $LD_{50}$ (mg/kg) |
|---|---|
| R-(+)-cyclophosphamide | 550 |
| S-(−)-cyclophosphamide | 330 |
| Racemic form of cyclophosphamide | 440 |

Absolute configurations indicated as the symbols "R" and "S" in the present specification are determined according to the disclosures of D. A. Adamai, K. R. Kinds, W. S. Saenber and W. J. Stec: Angew. Chem. Int. Ed., Engl., 16 330 (1977) and of I. L. Karle, I. M. Karle, W. Egan, G. Zon and J. A. Bandi: J. Am. Chem. Soc., 99, 4803 (1977).

Shown in the following are some examples of the present invention and reference examples in which preparations of R-(+)- or S-(−)-cyclophsphamide.

EXAMPLE 1

100 Milliliters of ether solution containing 7.8 g of phosphorus oxychloride is ice-cooled, and a solution prepared by dissolving 8.96 g of (S)-(−)-N-(3-hydroxypropyl)-α-phenylethylamine and 10.3 g of triethylamine in 50 ml of ether is added thereinto under stirring condition. The reaction is continued at the same temperature for 1 hour, then removing insoluble triethylamine hydrochloride by filtration. Filtrate thus obtained is concentrated under a reduced pressure to dryness to obtain 11 g of a mixture consisting of 2-(S)-3-[(S)-α-phenylethyl]tetrahydro-2-chloro-2H-1,3,2-oxyazaphosphorin 2-oxide and 2(R)-3-[(S)-α-phenylethyl]tetrahydro-2-chloro-2H-1,3,2-oxyazaphosphorin 2-oxide in the form of colorless crystals. The resulted mixture is determined by NMR spectrum to know that the ratio of the former to the latter is 8:1.

Said mixture is recrystallized from etherhexane to obtain 8 g of 2(S)-3-[(S)-α-phenylethyl]-tetrahydro-2-chloro-2H-1,3,2-oxyazaphosphorin 2-oxide in the form of colorless needle-like crystals.

Melting point: 71° to 73° C.; $[\alpha]_D^{25}$: +51.5° (C=8.2, ethanol).

Elemental analysis as $C_{11}H_{15}ClNO_2P$:

|  | C (%) | H (%) | N (%) | Cl (%) | P (%) |
|---|---|---|---|---|---|
| Calculated: | 50.88 | 5.82 | 5.40 | 13.65 | 11.93 |
| Found: | 51.80 | 5.80 | 5.18 | 13.72 | 11.85 |

The mother-liquor thus obtained in the above recrystallization is then concentrated and recrystallized from isopropylether to obtain 1.2 g of 2(R)-3-[(S)-α-phenylethyl]tetrahydro-2-chloro-2H-1,3,2-oxyazaphosphorin 2-oxide in the form of colorless prism like crystals.

Melting point: 69° to 71° C.; $[\alpha]_D^{25}$: −61.4° (C=3.01, ethanol).

Elemental analysis (as $C_{11}H_{15}ClNO_2P$)

|  | C (%) | H (%) | N (%) | Cl (%) | P (%) |
|---|---|---|---|---|---|
| Calculated: | 50.88 | 5.82 | 5.40 | 13.65 | 11.93 |
| Found: | 51.00 | 5.72 | 5.38 | 13.68 | 11.90 |

EXAMPLE 2

8.96 Grams of (R)-(+)-N-(3-hydroxypropyl)-α-phenylethylamine, 7.8 g of phosphorus oxychloride and 10.3 g of triethylamine are used by a procedure same as described in Example 1 to obtain 7.9 g of 2(R)-3-[(R)-α-phenylethyl]tetrahydro-2-chloro-2H-1,3,2-oxyazaphosphorin 2-oxide in the form of colorless needlelike crystals.

Melting point: 71° to 73° C.; $[\alpha]_D^{25}$: −51.6° (C=8.5, ethanol).

Elemental analysis (as $C_{11}H_{15}ClNO_2P$)

|  | C (%) | H (%) | N (%) | Cl (%) | P (%) |
|---|---|---|---|---|---|
| Calculated: | 50.88 | 5.82 | 5.40 | 13.65 | 11.93 |
| Found: | 50.98 | 5.76 | 5.45 | 13.68 | 11.95 |

By a procedure same as described in Example 1, 1.4 g of 2(S)-3-[(R)-α-phenylethyl]tetrahydro-2-chloro-2H-1,3,2-oxyazaphosphorin 2-oxide in the form of colorless prism-like crystals is obtained from the mother liquor of the recrystallization.

Melting point: 69° to 71° C.; $[\alpha]_D^{25}$: +61.6° (C=6.83, ethanol).

Elementary analysis (as $C_{11}H_{15}ClNO_2P$)

|  | C (%) | H (%) | N (%) | Cl (%) | P (%) |
|---|---|---|---|---|---|
| Calculated: | 50.88 | 5.82 | 5.40 | 13.65 | 11.93 |
| Found: | 51.01 | 5.75 | 5.36 | 13.69 | 11.91 |

EXAMPLE 3

3.22 Grams of phosphorus oxychloride is dissolved in 30 ml of toluene and placed in a flask. Said solution in the flask is cooled to −30° to −40° C. by using a mixture of dry ice-acetone bath, and 35 ml of a toluene solution, prepared by dissolving 5.35 g of (+)-N-(3-hydroxypropyl)-α-phenyl-β-(4-methylphenyl)ethylamine and 4.25 g of triethylamine, is added dropwise thereto during 20 minutes under stirring. Then the reaction mixture is stirred at the same temperature for 30 minutes and then stirred at a room temperature for 30 minutes. To the reaction mixture thus obtained is added 50 ml of water and 50 ml of ethyl acetate and separated into two liquid layers.

The aqueous layer is further extracted with ethyl acetate and the organic layers are combined. The combined organic layer is washed with water and then dried with magnesiun sulfate and then the solvent is removed by distillation under reduced pressure to obtain 7.0 g of colorless powdery solid substance.

According to NMR method, this substance contains two optical isomers in the ratio of 9:1.

The solid substance is recrystallized from a mixture of isopropyl ether and ethyl acetate (=30:50 v/v) to obtain 5.2 g (74.4%) of (+)-3-[α-phenyl-β-(4-methylphenyl)-ethyl]tetrahydro-2-chloro-2H-1,3,2-oxazaphosphorin 2-oxide in the form of colorless cotton like crystals.

M.P. 116.5°–118.5° C. $[\alpha]_D^{25}$: +122.5° (C=2.04, chloroform).

REFERENTIAL EXAMPLE 1

(a) 3.5 Grams of 2(S)-3-[(S)-α-phenylethyl]tetrahydro-2-chloro-2H-1,3,2-oxyazaphosphorin 2-oxide is dissolved in 35 ml of dioxane. Then 3 g of diethanolamine is added therein and refluxed for 2.5 hours. After removal of dioxane under a reduced pressure, the residue obtained is dissolved in methylene chloride and the solution is washed with a 15% aqueous solution of hydrochloric acid and an aqueous saturated solution of sodium chloride. The organic layer is separated and dried with anhydrous magnesium sulfate and filtered. The filtrated thus obtained is concentrated under a reduced pressure to dryness. The crystals thus obtained are crystallized from ethyl acetate to obtain 3.2 g of 2(S)-2-[bis(2-hydroxyethyl)amino]-3-[(S)-α-phenylethyl]tetrahydro-2H-1,3,2-oxyazaphosphorin 2-oxide in the form of colorless plate-like crystals.

Melting point: 104° to 106° C.; $[\alpha]_D^{25}$: −55.2° (C=6.54, ethanol).

Elementary analysis (as $C_{15}H_{25}N_2O_4P$)

|  | C (%) | H (%) | N (%) | P (%) |
|---|---|---|---|---|
| Calculated: | 54.87 | 7.67 | 8.53 | 9.41 |
| Found: | 55.18 | 7.53 | 8.42 | 9.38 |

(b) 3 Grams of thionyl chloride is dissolved in 10 ml of chloroform and is added dropwise a solution dissolving 3 g of 2(S)-2-[bis(2-hydroxyethylamino]-3-[(S)-α-phenylethyl]tetrahydro-2H-1,3,2-oxyazaphosphorin 2-oxide obtained in the above (a) under stirring at a room temperature then refluxed for 1 hours. After cooling the reaction mixture, the chloroform layer is washed with a saturated aqueous solutoin of sodium hydrogencarbonate and water in this order, then the chloroform layer is dried with anhydrous magnesium sulfate and filtered. The filtrate thus obtained is concentrated under a reduced pressure to obtain 3.1 g of 2(S)-2-[bis(2-chloroethyl)amino]-3-[(S)-α-phenylethyl]tetrahydro-2H-1,3,2-oxyazaphosphorin 2-oxide in the form of colorless oily substance.

$[\alpha]_D^{25}$: −62.4° (C=5.7, benzene)

IR spectrum and NMR spectrum of this compound are completely the same as those of the samples obtained by a method of Kinas [R. Kinas, K. Pankiemics and W. J. Stec: Bull. Acad. Polon. Sci., 23, 981 (1975)].

(c) 7.3 Grams of 2(S)-2-[bis(2-chloroethyl)-amino]-3-[(S)-α-phenylehtyl]tetrahydro-2H-1,3,2-oxyazaphosphorin 2-oxide is dissolved in 100 ml of ethanol and catalytically reduced in the presence of 800 mg of 10%-palladium charcoal under 20 atm. of hydrogen gas at 40°–45° C. After the reaction is completed, insoluble matters are removed off by filtration, and the filtrate is concentrated under a reduced pressure to obtain 4.6 g of crude crystals of R-(+)-cyclophosamide. Recrystallization from benzenehexane to obtain pure substance.

$[\alpha]_D^{25}: +2.32°$ (C=12.5, methanol).

The IR spectrum and NMR spectrum of this compound are identical to those of the sample obtained by a method of Kinas et al. and depression of melting point is not observed in mixed-sample test.

REFERENCE EXAMPLE 2

(a) 3.5 Grams of 2(R)-3-[(R)-α-phenylethyl]-tetrahydro-2-chloro-2H-1,3,2-oxazaphosphorin 2-oxide as obtained in the above Reference Example 1 and diethanolamine are reacted by a method similar to that of described in Reference Example 1-(a) to obtain 3.1 g of 2(R)-2-[bis(2-hydroxyethyl)amino]-3-[(R)-α-phenylethyl]tetrahydro-2H-1,3,2-oxazaphosphorin 2-oxide in the form of colorless plate-like crystals.

Melting point: 104° to 106° C. $[\alpha]_D^{25}: +56.1°$ (C=6.23, ethanol).

Elementary analysis (as $C_{15}H_{25}N_2O_4P$)

|  | C (%) | H (%) | N (%) | P (%) |
|---|---|---|---|---|
| Calculated: | 54.87 | 7.67 | 8.53 | 9.41 |
| Found: | 55.15 | 7.56 | 8.43 | 9.39 |

(b) 3.0 Grams of 2(R)-2-[bis(2-hydroxyethyl)-amino]-3-[(R)-α-phenylethyl]tetrahydro-2H-1,3,2,-oxazaphosphorin 2-oxide as obtained in the above Reference Example 2-(a) and 3 g of thionyl chloride are reacted by a method similar to that described in Reference Example 1-(b) to obtain 3.2 g of 2(R)-2-[bis(2-chloroethyl-)amino]-3-[(R)-phenylethyl]tetrahydro-2H-1,3,2-oxazaphosphorin 2-oxide in the form of an oily substance.

$[\alpha]_D^{25}: +63.4°$ (C=5.6 in benzene).

The IR spectrum and NMR spectrum of this compound are identical to those of the samples obtained by Kinas method.

(c) 7.3 Grams of 2(R)-2-[bis(2-chloroethyl)amino]-3-[(R)-α-phenylehtyl]tetrahydro-2H-1,3,2-oxazaphosphorin 2-oxide as obtained in Reference Example 2-(b) is catalytically reduced by a procedure as described in Reference Example 1-(c) to obtain 4.5 g of S(−)-cyclophosphamide in the form of colorless prism-like crystals.

Melting point: 65° to 66.5° C. $[\alpha]_D^{25}: -2.08°$ (C=12.5 in benzene).

The IR spectrum and NMR spectrum of this compound are identical to those of the sample obtained by method of Kinas et al. and further depression of melting point is not observed in mixed sample test.

What is claimed is:

1. A process for preparing an optically active oxazaphosphorin derivative represented by the general formula,

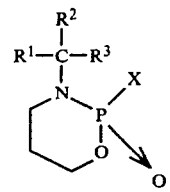

wherein $R^1$, $R^2$ and $R^3$ are respectively different from each other, and are each hydrogen atom, a lower alkyl group, an aralkyl group, or an aryl group; and X is a halogen atom, which is prepared by reacting an optically active aminoalcohol represented by the general formula,

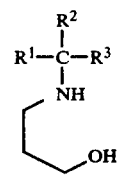

wherein $R^1$, $R^2$ and $R^3$ are the same as defined above with a phosphor compound represented by the general formula, $POX_3$ wherein X is a halogen atom.

2. A process according to claim 1, wherein the reaction is carried out in the absence or presence of a solvent.

3. A process according to claim 2, wherein the solvent is a saturated hydrocarbon, a halogenated aliphatic hydrocarbon, an aromatic hydrocarbon or an ether.

4. A process according to claim 3, wherein the saturated hydrocarbon is n-heptane, n-hexane, isooctane or cyclohexane.

5. A process according to claim 3, wherein the halogenated aliphatic hydrocarbon is methylene chloride, chloroform or 1,2-dichloroethane.

6. A process according to claim 3, wherein the aromatic hydrocarbon is benzene, toluene or xylene.

7. A process according to claim 3, wherein the ether is dimethylether, diethlether, isopropylether, tetrahydrofuran, dioxane, 1,2-dimethoxyethane, diglyme or triglyme.

8. A process according to claim 1, wherein the reaction is carried out in the presence of a basic compound.

9. A process according to claim 8, wherein the basic compound is a tertiary amine.

10. A process according to claim 9, wherein the tertiary amine is triethylamine, triisopropylamine, N,N-dimethylaniline, pyridine or quinoline.

11. A process according to claim 8, wherein the basic compound is an inorganic basic compound.

12. A process according to claim 11, wherein the inorganic basic compound is anhydrous potassium carbonate or anhydrous sodium carbonate.

13. A process according to claim 1, wherein the reaction is carried out at a temperature within the range from −70° to 100° C.

14. A process according to claim 13, wherein the reaction temperature is the range of from −70° to 50° C.

* * * * *